United States Patent
Truong

(10) Patent No.: US 11,242,505 B2
(45) Date of Patent: Feb. 8, 2022

(54) SELF-CONTAINED BIOLOGICAL INDICATOR

(71) Applicant: ASP GLOBAL MANUFACTURING GMBh, Schaffhausen OT (CH)

(72) Inventor: Doug Vo Truong, Irvine, CA (US)

(73) Assignee: ASP GLOBAL MANUFACTURING GMBH, Schaffhausen (CH)

( * ) Notice: Subject to any disclaimer, the term of this patent is extended or adjusted under 35 U.S.C. 154(b) by 52 days.

(21) Appl. No.: 15/397,018

(22) Filed: Jan. 3, 2017

(65) Prior Publication Data
US 2018/0187142 A1  Jul. 5, 2018

(51) Int. Cl.
*C12M 1/12* (2006.01)
*C12Q 1/22* (2006.01)
(Continued)

(52) U.S. Cl.
CPC ............... *C12M 37/06* (2013.01); *A61L 2/28* (2013.01); *C12M 23/38* (2013.01); *C12Q 1/22* (2013.01)

(58) Field of Classification Search
CPC ...................................................... C12M 37/06
See application file for complete search history.

(56) References Cited

U.S. PATENT DOCUMENTS 3,346,464 A  10/1967 Ernst
3,752,743 A  8/1973 Henshilwood
(Continued)

FOREIGN PATENT DOCUMENTS

CA   738687 A   7/1966
CA   823163 A   9/1969
(Continued)

OTHER PUBLICATIONS

NAMSA, Self-Contained Biological Indicators For Monitoring Steam (Northwood, Ohio 2015).
(Continued)

*Primary Examiner* — Jonathan M Hurst
(74) *Attorney, Agent, or Firm* — Etan S. Chatlynne; Roberts Calderon Safran & Cole P.C.

(57) ABSTRACT

A self contained biological indicator is disclosed having a housing and an ampule disposed within the housing, the ampule having a first dome, a second dome and a sidewall. A cap may be coupled to the housing. The cap may include a projection that may be coupled to the ampule by, e.g., a friction fit. An insert may be disposed within the housing. The insert may include a well within which at least a portion of the bottom dome of the ampule may be disposed. The insert may also include a ramp that is angled relative to the central longitudinal axis of the ampule. The second dome of the ampule may contact the ramp. The insert may also include an arm or finger that extends above the well and has a stress concentrator disposed thereon such that it is also disposed above the second dome of the ampule and adjacent to the sidewall of the ampule. In use, the SCBI generates therein a first reaction force between the second dome of the ampule and the ram having a component directed transverse to a central longitudinal axis of the ampule. The component of the first reaction force causes a second reaction force between the sidewall of the ampule and the stress concentrator. The second reaction force breaks the ampule.

19 Claims, 3 Drawing Sheets

(51) Int. Cl.
*A61L 2/28* (2006.01)
*C12M 1/00* (2006.01)

(56) References Cited

U.S. PATENT DOCUMENTS

| | | |
|---|---|---|
| 3,948,727 A | 4/1976 | Steiger |
| 4,291,122 A | 9/1981 | Orelski |
| 4,304,869 A | 12/1981 | Dyke |
| 4,528,268 A | 7/1985 | Andersen et al. |
| 4,546,086 A | 10/1985 | Hounsell |
| 4,717,661 A | 1/1988 | Mccormick et al. |
| 4,732,850 A * | 3/1988 | Brown .................. C12M 23/08 206/219 |
| 4,741,437 A | 5/1988 | Gorski et al. |
| 4,839,291 A * | 6/1989 | Welsh ...................... A61L 2/28 206/305 |
| 4,883,641 A | 11/1989 | Wicks et al. |
| 4,885,253 A | 12/1989 | Kralovic |
| 5,028,543 A | 7/1991 | Finch et al. |
| 5,073,488 A | 12/1991 | Matner et al. |
| 5,167,923 A | 12/1992 | Van Iperen |
| 5,223,401 A | 6/1993 | Foltz et al. |
| 5,252,484 A | 10/1993 | Matner et al. |
| 5,362,654 A | 11/1994 | Pouletty |
| 5,405,580 A | 4/1995 | Palmer |
| 5,415,994 A | 5/1995 | Imrich et al. |
| 5,418,167 A | 5/1995 | Matner et al. |
| 5,482,171 A | 1/1996 | Palmer |
| 5,516,648 A | 5/1996 | Malchesky et al. |
| 5,552,320 A | 9/1996 | Smith |
| 5,736,355 A | 4/1998 | Dyke et al. |
| 5,739,004 A | 4/1998 | Woodson |
| 5,750,184 A | 5/1998 | Imburgia |
| 5,759,848 A | 6/1998 | Nagoshi et al. |
| 5,770,393 A | 6/1998 | Dalmasso et al. |
| 5,801,010 A | 9/1998 | Falkowski et al. |
| 5,830,683 A | 11/1998 | Hendricks et al. |
| 5,863,790 A | 1/1999 | Bolea |
| 5,866,356 A | 2/1999 | Albert et al. |
| 5,942,438 A | 8/1999 | Antonoplos et al. |
| 6,218,189 B1 | 4/2001 | Antonoplos et al. |
| 6,436,659 B1 | 8/2002 | Hui et al. |
| 6,458,554 B1 | 10/2002 | Hui et al. |
| 6,551,555 B2 | 4/2003 | Antonoplos et al. |
| 6,924,139 B2 | 8/2005 | Eveland et al. |
| 7,091,042 B2 | 8/2006 | Lemus et al. |
| 7,247,482 B2 | 7/2007 | Lemus et al. |
| 7,642,067 B2 | 1/2010 | Song et al. |
| 8,173,388 B2 | 5/2012 | Pasmore et al. |
| 8,173,438 B1 | 5/2012 | Putnam et al. |
| 8,765,398 B2 | 7/2014 | Dalmasso |
| 8,840,837 B2 | 9/2014 | Smith et al. |
| 8,915,413 B2 | 12/2014 | Kayser |
| 8,945,837 B2 | 2/2015 | Franciskovich et al. |
| 8,969,029 B2 | 3/2015 | Chandrapati et al. |
| 8,980,622 B2 | 3/2015 | Smith |
| 9,145,573 B2 | 9/2015 | Pederson et al. |
| 9,322,046 B2 | 4/2016 | Chandrapati et al. |
| 9,675,722 B2 | 6/2017 | Ahimou et al. |
| 10,059,977 B2 | 8/2018 | Witcher et al. |
| 2004/0197848 A1 | 10/2004 | Behun et al. |
| 2005/0014214 A1 | 1/2005 | Eveland et al. |
| 2008/0070272 A1 | 3/2008 | Franciskovich et al. |
| 2009/0068716 A1 | 3/2009 | Hirota et al. |
| 2011/0200992 A1 | 8/2011 | Chandrapati et al. |
| 2012/0149094 A1 * | 6/2012 | Smith .................... C12Q 1/22 435/288.7 |
| 2012/0156090 A1 | 6/2012 | Dane et al. |
| 2013/0210048 A1 | 8/2013 | Chandrapati et al. |
| 2013/0217107 A1 | 8/2013 | Pederson et al. |
| 2013/0224849 A1 | 8/2013 | Chandrapati et al. |
| 2013/0273594 A1 | 10/2013 | Ahimou et al. |
| 2015/0004682 A1 | 1/2015 | Smith et al. |
| 2015/0167047 A1 | 6/2015 | Smith et al. |
| 2015/0337354 A1 | 11/2015 | Ahimou et al. |
| 2016/0000954 A1 | 1/2016 | Ahimou et al. |
| 2017/0175071 A1 | 6/2017 | Sullivan et al. |
| 2017/0211035 A1 | 7/2017 | Yirava et al. |
| 2017/0253845 A1 | 9/2017 | Amin |
| 2018/0015193 A1 | 1/2018 | Swaminathan et al. |
| 2018/0071421 A1 | 3/2018 | Fang et al. |
| 2018/0187142 A1 | 7/2018 | Truong |
| 2018/0237821 A1 | 8/2018 | Fryer |
| 2019/0002951 A1 | 1/2019 | Fryer et al. |
| 2019/0106725 A1 | 4/2019 | Cregger et al. |
| 2019/0106726 A1 | 4/2019 | Cregger et al. |
| 2019/0169672 A1 | 6/2019 | Fryer et al. |

FOREIGN PATENT DOCUMENTS

| | | |
|---|---|---|
| CA | 1 182 729 A | 2/1985 |
| CN | 18553734 A | 11/2006 |
| CN | 201453688 U | 5/2010 |
| CN | 102596261 A | 7/2012 |
| CN | 203307339 U | 11/2013 |
| CN | 105087361 A | 11/2015 |
| CN | 204814967 U | 12/2015 |
| CN | 105561362 A | 5/2016 |
| CN | 106267277 A | 1/2017 |
| CN | 206473580 U | 9/2017 |
| CN | 206970617 U | 2/2018 |
| EP | 0152298 A2 | 8/1985 |
| EP | 1032822 B1 | 5/2003 |
| EP | 2968634 B1 | 12/2016 |
| FR | 2708287 B1 | 10/1995 |
| GB | 1055389 A | 1/1967 |
| JP | 10201466 A | 8/1998 |
| JP | 11196893 A | 7/1999 |
| JP | 2017123976 A | 7/2017 |
| JP | 2018201397 A | 12/2018 |
| RU | 129814 U1 | 7/2013 |
| RU | 143648 U1 | 7/2014 |
| RU | 146719 U1 | 10/2014 |
| RU | 2683644 C2 | 4/2019 |
| WO | 92/19764 A1 | 11/1992 |
| WO | 97/35189 A1 | 9/1997 |
| WO | 00/50634 A1 | 8/2000 |
| WO | 2005/036128 A2 | 4/2005 |
| WO | 2010/039388 A2 | 4/2010 |
| WO | 2010/045138 A2 | 4/2010 |
| WO | 2016/057520 A1 | 4/2016 |
| WO | 2016/205953 A1 | 12/2016 |
| WO | 2018025207 A1 | 2/2018 |
| WO | 2018/160449 A1 | 9/2018 |
| WO | 2008106327 A2 | 9/2018 |
| WO | 2020/136463 A1 | 7/2020 |

OTHER PUBLICATIONS

Anonymous, 3M™ Attest™ 1292E Rapid Readout Biological Indicator, Internet Article, Jan. 1, 1999, http://multimedia.3m.com/mws/mediawebserver?mwsld=SSSSSu7zK1fslxtU48_el8mGev7qe17zHvTSevTSeSSSSSS--&fn=Rapid_Readout_Profile_1292E.pdf.
Chinese First Office Action and Search Report for Chinese Patent Application No. 201810004516.1 dated Aug. 3, 2020 and English translation.
Russian Search Report for Registration No. 2017145872/04(078515) dated Dec. 26, 2017, Date of valid search completion: Jun. 10, 2021, 2 pages.
PCT Notification of Transmittal of the International Search Report and the Written Opinion of the International Searching Authority, or the Declaration for International Application No. PCT/IB2020/058750 dated Nov. 27, 2020, 1 page.
PCT Written Opinion of the International Searching Authority for International Application No. PCT/IB2020/058750 dated Nov. 27, 2020, 6 pages.
PCT International Search Report for International Application No. PCT/IB2020/058750 dated Nov. 27, 2020, 6 pages.

\* cited by examiner

SELF-CONTAINED BIOLOGICAL INDICATOR

FIELD

The subject matter disclosed herein relates to self-contained biological sterilization indicators.

BACKGROUND

Medical devices are typically sterilized before use in order to minimize the likelihood that a contaminated device might be used on a subject, which could cause an infection in the subject. Various sterilization techniques may be employed, such as steam, hydrogen peroxide, and vapor phase sterilization, either with or without a gas plasma and ethylene oxide (EtO). Each of these methods depends to a certain extent on the diffusion rates of the sterilization fluids, typically gases, upon the medical devices to be sterilized.

Before sterilization, medical devices are typically packaged within containers or pouches having a semi-permeable barrier that allows transmission of the sterilizing fluid—sometimes referred to as a sterilant—but prevents admission of contaminating organisms, particularly post-sterilization and until the package is opened by medical personnel. For the sterilization cycle to be efficacious, the contaminating organisms within the package must be killed because any organisms that survive the sterilization cycle could multiply and re-contaminate the medical device.

Although the packaging helps prevent contamination of a sterile medical device, the packaging may increase the difficulty of achieving a successful sterilization cycle because the packaging impedes the sterilant from reaching the device or instrument contained therein. This is particularly problematic for devices and instruments that have diffusion-restricted spaces therein because these diffusion-restricted spaces reduce the likelihood that a sterilization cycle may be effective. For example, endoscopes typically have long narrow lumens into which the sterilant must diffuse in sufficient concentration for sufficient time to achieve a successful sterilization cycle.

Confirming that a sterilization cycle has been efficacious helps medical personnel avoid using a contaminated medical device on a subject. Typically, the sterilized medical device is not itself checked for contaminating organisms because such an activity would introduce other contaminating organisms to the medical device, thereby re-contaminating it. Thus, an indirect check has been developed in the form of a sterilization indicator.

A sterilization indicator is a device that may be placed alongside or in proximity to a medical device being subject to a sterilization cycle, such that the sterilization indicator is subject to the same sterilization cycle as the medical device. For instance, a biological indictor having a predetermined quantity of microorganisms possessing known resistance to the sterilant may be placed into a sterilization chamber alongside a medical device and subjected to a sterilization cycle. After the cycle is complete, the microorganisms in the biological indicator may be cultured to determine whether any of the microorganisms survived the cycle.

Certain biological indicators are referred to as being "self-contained." These biological indicators typically include a housing that contains a quantity of microorganisms and a source of growth media in a frangible container that is located near the microorganisms. Like other biological indicators, the "self-contained" biological indicator ("SCBI") may be subject to a sterilization cycle alongside medical devices. Following the cycle, the frangible container may be broken to release the growth media and culture any surviving microorganisms in situ. The SCBI may be incubated at elevated temperatures, typically around 50° C. to 60° C., which encourages outgrowth of the surviving microorganisms. Incubation using commercially available products typically lasts for about twenty-four hours. During this time, while the effectiveness of the sterilization remains unconfirmed, it is desirable that medical personnel do not use the medical devices. This may cause inventory management inefficiencies for a health care provider, such as a hospital, because, for example, the medical devices should be stored while they cannot be used, perhaps requiring the health care provider to keep more medical devices in its inventory than it otherwise would to ensure a sufficient supply of medical devices. Alternatively, health care providers may use the medical devices before the incubation is completed and sterilization efficacy confirmed. However, using the medical devices before sterilization efficacy has been confirmed may expose a subject of a medical procedure to risk of infection from the medical devices.

After incubation, the SCBI is analyzed to detect the presence of microorganisms. Should any microorganisms be detected, some SCBIs are designed to incorporate a growth medium that changes color in the presence of microorganisms. If a color change is detected, the sterilization cycle may be considered to have been ineffective. Should no microorganisms be detected, the sterilization cycle may be considered to have been effective. This color change may be due to a shift in pH that occurs due to acid production by live microorganisms that metabolize a growth medium, which also contains a pH indicating dye. Other SCBIs are designed to incorporate a growth medium that includes a fluorophore whose fluorescence depends on the amount of viable microorganisms contained in the medium. For these SCBIs, a color change or change in the amount of fluorescence indicates that surviving microorganisms may have multiplied during incubation.

The frangible container of the SCBI that contains the liquid growth medium is often fabricated from glass. The glass must be sufficiently robust to avoid breakage during transportation, e.g., from the manufacturer of the SCBI to a health care provider. Such robustness, however, corresponds to a greater force required to break the ampule at the desired time by medical personnel. Accordingly, some SCBI manufacturers provide activation devices to hospital personnel to assist them in breaking the ampule.

SUMMARY

An SCBI is disclosed that in some embodiments includes a housing and an ampule disposed within the housing, the ampule having a first dome, a second dome and a sidewall. A cap may be coupled to the housing. The cap may include a projection that may be coupled to the ampule by, e.g., a friction fit. The projection is centered on the cap such that a central longitudinal axis of the ampule, a central longitudinal axis of the cap, and a central longitudinal axis of the housing are substantially aligned. An insert may be disposed within the housing. The insert may include a well within which at least a portion of the bottom dome of the ampule may be disposed. The insert may also include a ramp that is angled at least 5 degrees relative to the central longitudinal axis of the ampule. The second dome of the ampule may contact the ramp. The insert may also include an arm or finger that extends above the well and has a stress concentrator disposed thereon such that it is also disposed above the second dome of the ampule and adjacent to the sidewall of the ampule.

In some embodiments, the ramp and the stress concentrator are configured to restrict movement of the ampule away from the cap along the central longitudinal axis of the ampule. In some embodiments the stress concentrator has a pointed tip. In some embodiments the stress concentrator has a rounded tip. In some embodiments the stress concentrator may be disposed at least approximately 5 mm above the second dome. In some embodiments the stress concentrator may be disposed at least approximately 10 mm above the second dome. In some embodiments the stress concentrator spans an arc of at least approximately 5 degrees. In some embodiments the stress concentrator spans an arc of at least 15 degrees. In some embodiments the ramp spans an arc of at least approximately 30 degrees. In some embodiments the ramp spans an arc of at least approximately 50 degrees. In some embodiments the insert has a circular shape such that a midpoint of an arc spanned by the ramp and a midpoint of an arc spanned by the stress concentrator are collinear with a diameter of the insert. In some embodiments the ampule does not contact the housing. In some embodiments the stress concentrator contacts the sidewall of the ampule.

Also disclosed herein are steps that may be performed to activate an SCBI. These steps include: a) generating a first reaction force between a dome of an ampule and an angled surface wherein a component of the first reaction force is directed transverse to a central longitudinal axis of the ampule; b) generating a second reaction force between a sidewall of the ampule and a stress concentrator in response to the component of the first reaction force; and c) breaking the ampule. The step of breaking the ampule may include initiating a crack at a point of contact between the stress concentrator and the sidewall of the ampule. Further, the first reaction force may be generated by applying a compressive force between a cap and a housing of the SCBI.

The SCBI that may be used to perform the foregoing steps may include a stress concentrator that is a feature of an insert and that is configured to contact the sidewall of the ampule. The insert of the SCBI may include no more than one stress concentrator. The angled surface of the SCBI may be a feature of the insert. The insert may be disposed within the housing of the SCBI. The ampule may rest upon the angled surface before the reaction force is generated. The cap may be coupled to the housing and it may also be coupled to the ampule by a friction fit. The ampule cannot contact the housing.

As used herein, the term "surface" should be understood as a feature of an object that forms a boundary of the object.

As used herein, the term "wall" should be understood as a feature of an object that forms at least a portion of a side, top, or bottom, of that object. A wall is an example of a surface.

As used herein, the term "insert" should be understood as an object that is disposed within a space or cavity defined by another object.

As used herein, the terms "arm," "finger," "leg," and "projection" should each be understood as an elongate member of an object that originates at and extends away from another feature of that object.

As used herein, the term "carrier" should be understood as an object upon which microorganisms and/or enzymes have been disposed.

As used herein, the term "reaction force" should be understood as a force generated by an object in response to another force on the object, where at least a component of the reaction force points in a direction opposite to the direction of the another force.

As used herein, the term "stress concentrator" should be understood as a feature that includes a surface area configured to exert a reaction force against an object, where the surface area configured to exert the reaction force is less than a surface area of the object upon which another force is exerted.

As used herein, the term "friction fit" should be understood as a coupled relationship between two or more surfaces that is achieved by friction.

BRIEF DESCRIPTION OF THE DRAWINGS

While the specification concludes with claims which particularly point out and distinctly claim the subject matter described herein, it is believed the subject matter will be better understood from the following description of certain examples taken in conjunction with the accompanying drawings, in which like reference numerals identify the same elements and in which:

DETAILED DESCRIPTION

The following description sets forth certain illustrative examples of the claimed subject matter. Other examples, features, aspects, embodiments, and advantages of the technology should become apparent to those skilled in the art from the following description. Accordingly, the drawings and descriptions should be regarded as illustrative in nature.

Figure 1:
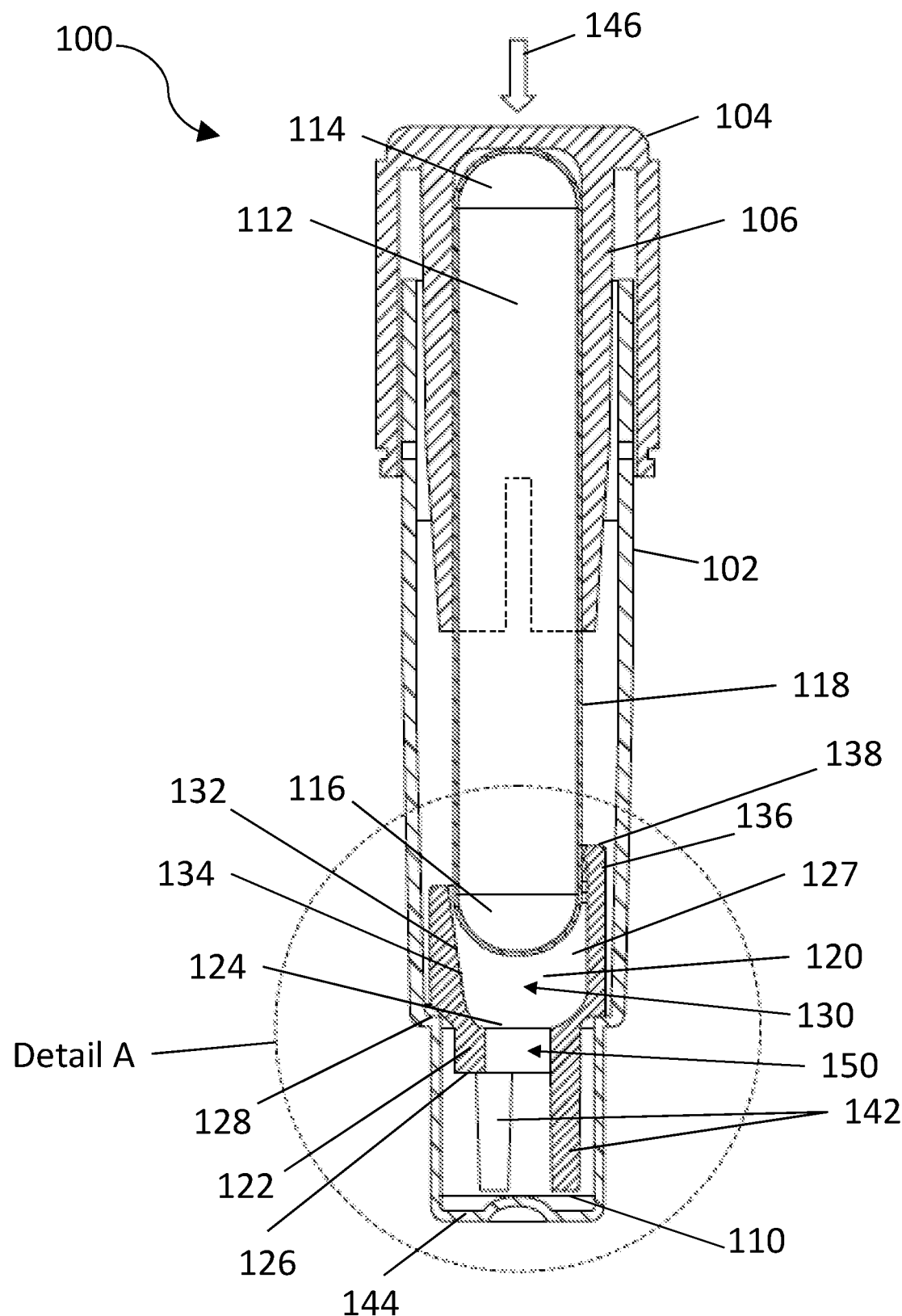
FIG. 1 depicts a side section view of an SCBI.
Figure 2:
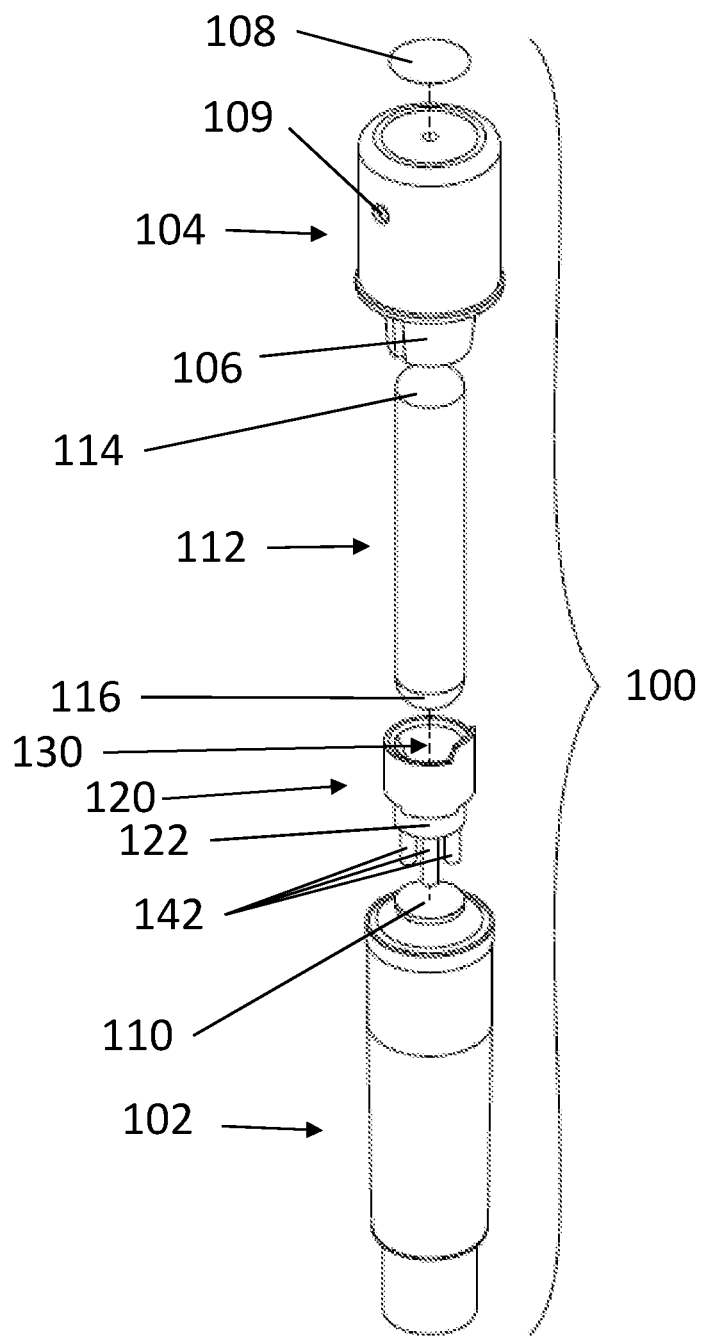
FIG. 2 depicts an isometric exploded view of the SCBI.
Figure 3:
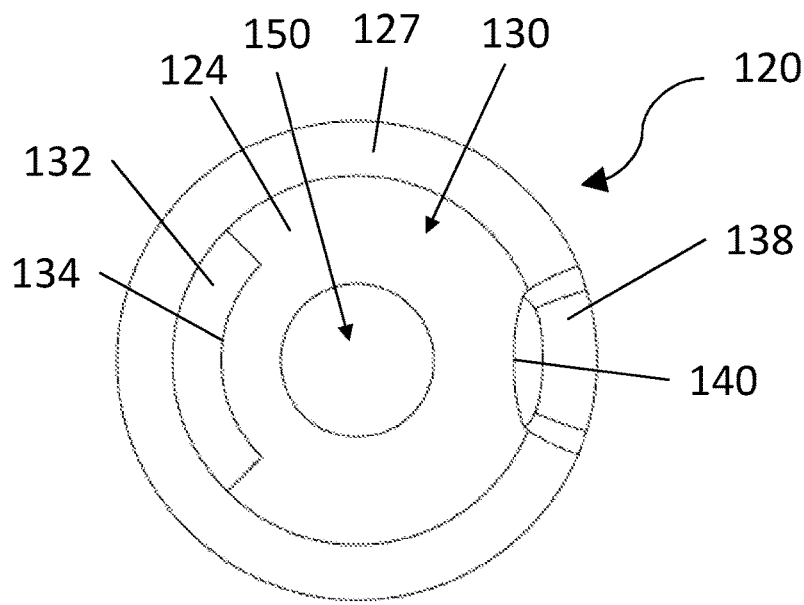
FIG. 3 depicts a top view of an insert of the SCBI.
Figure 4:
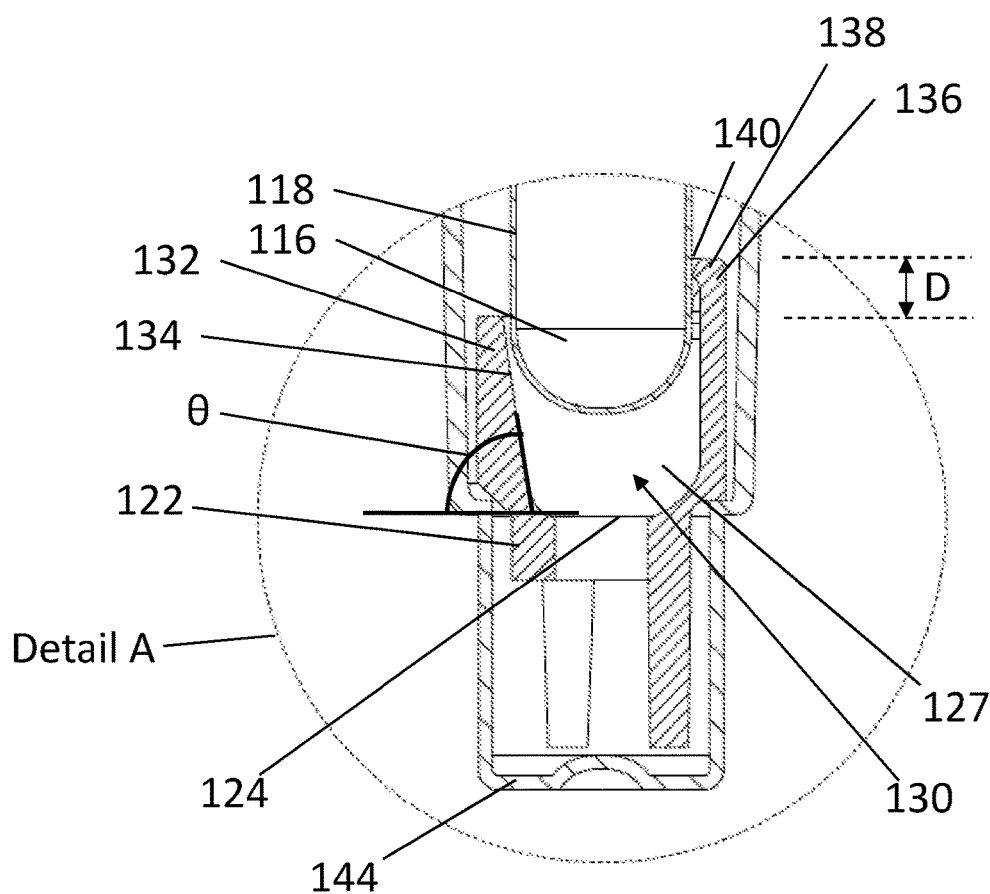
FIG. 4 depicts a detail view for a portion of the section view of FIG. 1.

Referring to FIGS. 1 and 2, a self-contained biological indicator ("SCBI") 100 is shown. SCBI 100 includes a housing 102 and a cap 104 coupled thereto. Cap 104 includes a projection 106 that has a planar, angled, arcuate, annular, or conical shape, or some combination thereof. Cap 104 may further include a chemical indicator 108 that changes color when exposed to, e.g., a chemical sterilant such as hydrogen peroxide. Cap 104 may also include one or more through-holes 109, to assist in the passage of gasses (e.g., air or sterilant) into or out from the SCBI. Cap 104 is coupled relative to housing 102 in a first position and is movable from the first position to a second position. In the first position (shown in FIGS. 1 and 2), Cap 104 is coupled to housing 102 in a manner in which gases (e.g., air or sterilant) may move from the surrounding environment and into the SCBI, or vice versa. In this position, any through-holes in cap 104 are disposed above housing 102 such that the inside of housing 102 is in fluid communication with the surrounding environment, which permits introduction and withdrawal of sterilant into and from SCBI 100. Cap 104 may be depressed to move it into the second position relative to housing 102. In this second position, through-holes 109 are disposed below a top end of housing 102, which causes a tight fitting relationship between housing 102 and cap 104, and blocks the through holes, effectively sealing off the inside of the SCBI 100 from the surrounding environment.

SCBI 100 also includes a source of microorganisms or active enzymes, such as carrier 110, which is impregnated with bacterial spores, other forms of bacteria (e.g., vegetative), and/or active enzymes. Spores from *Bacillus, Geobacillus,* and *Clostridia* species are often used to monitor sterilization processes utilizing saturated steam, hydrogen peroxide, dry heat, gamma irradiation and ethylene oxide. Accordingly, carrier 110 may be impregnated with spores from *Bacillus, Geobacillus*, and/or *Clostridia* species. Carrier 110 may be water-absorbent and may be formed of filter paper. Sheet-like materials such as cloth, nonwoven polypropylene, rayon or nylon, and microporous polymeric materials may also be used. Non-water absorbent materials are also appropriate for use, such as metals (e.g., aluminum or stainless steel), glass (e.g., glass beads or glass fibers), porcelain, or plastic. Additionally, carrier 110 can be constructed of a combination of the aforementioned materials. In some embodiments, carrier 110 may have a thickness of approximately 0.1 to 0.5 millimeters.

SCBI 100 also includes an ampule 112, having a first end 114, a second end 116, and a sidewall 118. Sidewall 118 is substantially cylindrical and may have an elliptical or circular cross section. First end 114 and second end 116 dome are disposed at opposite ends of sidewall 118, and may have the form of a hemiellipsoid or hemisphere. Accordingly, first end 114 may be referred to as first dome 114 and second end 116 may be referred to as second dome 116. Ampule 112 contains a liquid growth medium. The growth medium should be capable of promoting growth of any viable microorganisms disposed on carrier 110. Growth may be accelerated by incubation at elevated temperatures, e.g., between approximately 50° C. and 60° C. Ampule 112 may be fabricated from a frangible or brittle material such as glass or plastic.

SCBI 100 may also include an insert 120, which is shown in FIGS. 1-4. Insert 120 may include a platform 122 having a top surface 124 and a bottom surface 126. Insert 120 also includes a sidewall 127. Sidewall 127 of platform 122 may rest upon a support surface 128, which may be integrally formed as part of housing 102. Sidewall 127 and top surface 124 of platform 122 together define a well 130, which is configured to receive second end 116 of ampule 112. Platform 122 defines a bore 150 therethrough, through which the liquid growth medium may pass upon breakage of the ampule.

Insert 120 further includes a ramp 132. Ramp 132 is disposed upon or formed as an integral feature of sidewall 127. Ramp 132 includes an angled surface or ramp surface 134. Ramp surface 134 and top surface 124 of platform 122 are disposed in an angular relationship. As shown in FIG. 4, ramp surface 134 is disposed at θ degrees with respect to platform top surface 124. θ may be equal to approximately 85 degrees, 80 degrees, 75 degrees, 70 degrees, or less.

Insert 120 also includes a finger (arm) 136 that extends above well 130 of insert 120. Finger 136 is disposed opposite ramp 132. Disposed upon finger 136, facing ramp 132, is a stress concentrator 138. Stress concentrator 138 may include a tip 140. Tip 140 may be pointed. It may have a triangular configuration. Tip 140 may alternatively have a rounded configuration. Tip 140 is spaced a distance D above sidewall 127. D may be equal to approximately between 1 mm and 25 mm, between approximately 1 mm and 15 mm, between approximately 1 mm and 5 mm, or it may be between approximately 1-3 mm.

Ramp 132 is disposed along sidewall 127 within well 130 while finger 136 extends upward from sidewall 127. Accordingly, both ramp 132 and finger 136 may have arcuate configurations having curvatures similar to the curvature of sidewall 127. In some embodiments, a midpoint of the arc of ramp 132 and a midpoint of the arc of finger 136 are collinear with a diameter of insert 120. In some embodiments, the arc of ramp 132 spans at least approximately 30 degrees. In some embodiments, the arc of ramp 132 spans at least approximately 50 degrees. In some embodiments, the arc of finger 136 spans at least approximately 15 degrees. In some embodiments, the arc of finger 136 spans at least approximately 30 degrees.

Insert 120 may also include a leg (or legs) 142 that originates from bottom surface 126 of platform 122 and extends away therefrom. Leg 142 has a maximum length equal to the distance between support surface 128 and a bottom wall 144 of housing 102. As shown in FIG. 4, leg 142 has a length that is somewhat less than the distance between support surface 128 and bottom wall 144. Leg 142 may have a length that is approximately 0.1 to 1 millimeter less than the distance between support surface 128 and bottom wall 144. Insert 120 may include multiple instances of leg 142. For example, insert 120 may include three instances of leg 142. Leg or legs 142 function to maintain carrier 110 against bottom wall 144 to help prevent carrier 110 from becoming damaged or dislodged during transportation.

SCBI 100 may be assembled according to the following steps. First, housing 102 is provided. Second, carrier 110 is placed into housing 102 such that it rests upon bottom wall 144 of housing 102. Third, insert 120 is placed into housing 102 such that sidewall 127 of platform 122 rests upon support surface 128. Alternatively, not shown, in some configurations lacking a support surface 128, insert 120 may rest directly upon bottom wall 142 and may be in at least partial contact with carrier 110. Fourth, ampule 112 is inserted into housing 102 such that second end 116 contacts ramp 132. Finally, cap 104 is coupled to housing 102 and ampule 112. Projection 106 has approximately the same diameter as ampule 112 such that a friction fit is formed between ampule 112 and projection 106. So assembled, central longitudinal axes of ampule 112, housing 102, cap 104, and insert 120 are coaxial or substantially coaxial. Other assembly procedures may be performed to achieve the same configuration of SCBI 100.

The configuration of SCBI 100, and in particular, the relationships between its various components, maintain ampule 112 in a stationary state, which helps prevent premature breakage of ampule 112, e.g., during transportation from a manufacturing facility to a healthcare facility. For example, cap 104, ramp 132 and stress concentrator 138 prevent ampule 112 from moving away from cap 104 or moving in a lateral direction within housing 102. In some configurations, ampule 112 may contact tip 140. In other configurations, there may be spacing between ampule 112 and tip 140.

Because the central longitudinal axes of ampule 112 and insert 120 are coaxial, ramp 132 is disposed at an angle φ to ampule 112 where φ equals 90 degrees minus θ. Accordingly, φ may be equal to approximately 5 degrees, 10 degrees, 15 degrees, 20 degrees, or more.

Following a sterilization procedure, an SCBI may be activated and monitored to determine whether a sterilization cycle was effective. To activate SCBI 100, a compressive force 146 is applied between housing 102 and cap 104. This compressive force is resisted by ampule 112 because ampule 112 is in contact with ramp 132 of insert 120 and insert 120 is in contact with, e.g., support 128 of housing 102. When the compressive force applied to cap 104 is greater than a breakage force ampule 112 can withstand, ampule 112 will break. Once ampule 112 is broken, cap 104 moves to its second position and growth medium is released to immerse carrier 110.

The specific breakage mechanism of ampule 112 provided by SCBI 100 lowers the magnitude of the compressive force that must be applied to cap 104 to break ampule 112. Specifically, the compressive downward force applied to cap 104 causes a first reaction force at the point of contact between second end 116 of ampule 112 and ramp 132 of insert 120. This reaction force is perpendicular to ramp surface 134. Accordingly, this reaction force includes a component that is substantially parallel to the central longitudinal axis of ampule 112 and a component that is substantially perpendicular or transverse to the central longitudinal axis of ampule 112. The transverse component causes sidewall 118 of ampule 112 to press against stress concentrator 138, or more specifically tip 140 of stress concentrator 138, which causes a second reaction force against sidewall 118 that is transverse to the central longitudinal axis of ampule 112. The magnitude of this reaction force may be approximated as the magnitude of the force applied to the cap multiplied by $\tan(\varphi)$. As the magnitude of the compressive force applied to cap 104 increases, so too does the magnitude of the first reaction force and the second reaction force until the second reaction force becomes greater than the ampule can withstand, which causes the ampule to break. Because the second reaction force is applied laterally to sidewall 118, the breakage is initiated at the point of contact between stress concentrator 138 and sidewall 118. Initial cracks may be formed at or near this point of contact before the ampule breaks. When ampule 112 is fabricated from glass, formation of the initial crack or cracks is promptly followed by the glass shattering into many shards. These shards collect upon insert 120, allowing the growth medium to flow through and alongside insert 120 to immerse carrier 110.

Before activation of SCBI 100, first end 114 of ampule 112 is maintained within projection 106 of cap 104 and second end 116 of ampule 112 is maintained within well 130, between ramp 132 and stress concentrator 138. This configuration has two beneficial purposes. First, this configuration minimizes the magnitude of the compressive force that must be applied to the cap to break the ampule because the compressive force presses ampule 112 against ramp 132, which removes the collinear relationship between the longitudinal axis of ampule 112 and the longitudinal axis of insert 120. Accordingly, stress concentrator 138 presses against sidewall 118 in an asymmetric manner, which increases the stresses in ampule 112, in part by avoiding generation of internal stresses that cancel each other, thereby facilitating breakage of ampule 112. Second, this configuration restricts movement of the ampule within the SCBI, which minimizes rattling and jostling of ampule 112 within SCBI 100 and helps avoid premature breakage of the ampule, e.g., during transportation.

It should be understood that any of the examples and/or embodiments described herein may include various other features in addition to or in lieu of those described above. The teachings, expressions, embodiments, examples, etc. described herein should not be viewed in isolation relative to each other. Various suitable ways in which the teachings herein may be combined should be readily apparent to those of ordinary skill in the art in view of the teachings herein.

Having shown and described exemplary embodiments of the subject matter contained herein, further adaptations of the methods and systems described herein may be accomplished by appropriate modifications without departing from the scope of the claims. Some such modifications should be apparent to those skilled in the art. For instance, the examples, embodiments, geometrics, materials, dimensions, ratios, steps, and the like discussed above are illustrative. Accordingly, the claims should not be limited to the specific details of structure and operation set forth in the written description and drawings.

I claim:

1. A biological sterilization indicator comprising:
   (a) a housing;
   (b) an ampule disposed within the housing, the ampule having a first dome, a second dome, and a sidewall;
   (c) a cap coupled to the housing, the cap having a projection coupled to the ampule by a friction fit such that a longitudinal axis of the ampule and a longitudinal axis of the housing are coaxially aligned; and
   (d) an insert disposed within the housing, the insert comprising
      (i) a sidewall defining a well within which at least a portion of the second dome is disposed;
      (ii) a ramp disposed in the well along the sidewall, the ramp having a ramp surface that is angled at least 5 degrees relative to the longitudinal axis of the ampule and in contact with the second dome of the ampule; and
      (iii) a stress concentrator disposed above the well and adjacent to the sidewall of the ampule.

2. The biological sterilization indicator of claim 1 wherein the insert further comprises an arm extending above the well, the stress concentrator being disposed on the arm.

3. The biological sterilization indicator of claim 1 wherein the ramp and the stress concentrator are configured to restrict movement of the ampule away from the cap along the longitudinal axis of the ampule.

4. The biological sterilization indicator of claim 1 wherein the stress concentrator includes tip.

5. The biological sterilization indicator of claim 4 wherein the tip comprises a rounded configuration.

6. The biological sterilization indicator of claim 4 wherein the tip is disposed at least approximately 5 mm above the sidewall.

7. The biological sterilization indicator of claim 6 wherein the tip is disposed at least approximately 10 mm above the sidewall.

8. The biological sterilization indicator of claim 1 wherein the stress concentrator spans an arc of at least approximately 5 degrees.

9. The biological sterilization indicator of claim 1 wherein the stress concentrator spans an arc of at least approximately 15 degrees.

10. The biological sterilization indicator of claim 9 wherein the stress concentrator spans an arc of at least approximately 30 degrees.

11. The biological sterilization indicator of claim 1 wherein the ramp spans an arc of at least approximately 30 degrees.

12. The biological sterilization indicator of claim 11 wherein the ramp spans an arc of at least approximately 50 degrees.

13. The biological sterilization indicator of claim 1 wherein the insert has circular shape and wherein a midpoint of an arc spanned by the ramp and a midpoint of an arc spanned by the stress concentrator are collinear with a diameter of the insert.

14. The biological sterilization indicator of claim 1 wherein the ampule does not contact the housing.

15. The biological sterilization indicator of claim 1 wherein the stress concentrator contacts the sidewall of the ampule.

16. The biological sterilization indicator of claim 1, further comprising a carrier disposed on a bottom wall of the housing, the carrier including a source of microorganisms or active enzymes.

17. The biological sterilization indicator of claim 16, wherein the insert further comprises a bottom surface and a leg that originates from the bottom surface and extends toward the bottom wall of the housing.

18. The biological sterilization indicator of claim 17, the leg comprises a first leg and the insert further comprises a second leg that originates from the bottom surface and extends toward the bottom wall of the housing and a third leg that originates from the bottom surface and extends toward the bottom wall of the housing.

19. The biological sterilization indicator of claim 4, wherein the tip comprises a triangular configuration.

\* \* \* \* \*